United States Patent
Lunn et al.

(10) Patent No.: US 9,649,104 B2
(45) Date of Patent: May 16, 2017

(54) ANCHOR

(71) Applicant: Smith & Nephew, Inc., Memphis, TN (US)

(72) Inventors: Richard M. Lunn, Kingston, MA (US); David A. Paulk, Hopedale, MA (US)

(73) Assignee: Smith & Nephew, Inc., Memphis, TN (US)

( * ) Notice: Subject to any disclaimer, the term of this patent is extended or adjusted under 35 U.S.C. 154(b) by 408 days.

(21) Appl. No.: 14/582,660

(22) Filed: Dec. 24, 2014

(65) Prior Publication Data

US 2015/0119937 A1    Apr. 30, 2015

Related U.S. Application Data

(62) Division of application No. 13/736,586, filed on Jan. 8, 2013, now Pat. No. 8,951,292, which is a division of application No. 12/503,394, filed on Jul. 15, 2009, now Pat. No. 8,372,124.

(60) Provisional application No. 61/081,438, filed on Jul. 17, 2008.

(51) Int. Cl.
    A61B 17/04    (2006.01)

(52) U.S. Cl.
    CPC .... *A61B 17/0401* (2013.01); *A61B 2017/044* (2013.01); *A61B 2017/0409* (2013.01); *A61B 2017/0414* (2013.01); *A61B 2017/0424* (2013.01); *A61B 2017/0464* (2013.01)

(58) Field of Classification Search
    CPC ........ A61B 17/0401; A61B 2017/0409; A61B 2017/0414; A61B 2017/044
    See application file for complete search history.

(56) References Cited

U.S. PATENT DOCUMENTS

| 5,243,300 A | 9/1993 | Kubo |
| 5,423,860 A | 6/1995 | Lizardi et al. |
| 5,472,452 A | 12/1995 | Trott |
| 5,480,403 A | 1/1996 | Lee et al. |

(Continued)

FOREIGN PATENT DOCUMENTS

| WO | 02/21999 A | 3/2002 |
| WO | 2006099109 A2 | 9/2006 |

(Continued)

OTHER PUBLICATIONS

European Patent Office Communication regarding Application No. 09 790 456.9-1528, mailed on Jun. 8, 2012.

(Continued)

*Primary Examiner* — Nicholas Woodall
(74) *Attorney, Agent, or Firm* — Burns & Levinson LLP; Joseph M. Maraia

(57) ABSTRACT

The present disclosure relates to an anchor. The anchor includes an outer member including a body having an inner cavity, wherein the inner cavity includes a proximal portion configured for receipt of a delivery device and a distal portion having area of increased diameter. The anchor also includes an inner member coupled to the outer member, wherein the inner member includes a proximal portion having a projection configured for receipt in the area of increased diameter and a distal portion having a transverse through hole. A delivery device and method for tissue repair are also disclosed.

1 Claim, 6 Drawing Sheets

(56) References Cited

U.S. PATENT DOCUMENTS

| | | |
|---|---|---|
| 5,486,197 A | 1/1996 | Le et al. |
| 5,723,013 A | 3/1998 | Jeanson et al. |
| 5,725,529 A | 3/1998 | Nicholson et al. |
| 5,733,307 A | 3/1998 | Dinsdale |
| 5,957,953 A | 9/1999 | DiPoto et al. |
| 6,048,344 A | 4/2000 | Schenk |
| 6,517,542 B1 | 2/2003 | Papay et al. |
| 6,544,281 B2 | 4/2003 | Elattrache et al. |
| 6,554,830 B1 | 4/2003 | Chappius |
| 6,641,596 B1 | 11/2003 | Lizardi |
| 2002/0147463 A1 | 10/2002 | Martinek |
| 2004/0138706 A1 | 7/2004 | Abrams |
| 2004/0220575 A1 | 11/2004 | Biedermann et al. |
| 2005/0075668 A1 | 4/2005 | Lizardi |
| 2005/0245932 A1 | 11/2005 | Fanton et al. |
| 2006/0235413 A1 | 10/2006 | Denham |
| 2006/0247642 A1 | 11/2006 | Stone et al. |
| 2006/0271054 A1 | 11/2006 | Sucec |
| 2006/0276841 A1 | 12/2006 | Barbieri et al. |
| 2007/0162025 A1 | 7/2007 | Tornier et al. |
| 2007/0219557 A1 | 9/2007 | Bourque |
| 2008/0009904 A1* | 1/2008 | Bourque ............ A61B 17/0401 606/232 |
| 2008/0125815 A1* | 5/2008 | Heaven ............ A61B 17/0401 606/308 |
| 2008/0249579 A1 | 10/2008 | Taylor |
| 2013/0197577 A1* | 8/2013 | Wolf ................. A61B 17/0401 606/232 |

FOREIGN PATENT DOCUMENTS

| | | |
|---|---|---|
| WO | 2006122218 A2 | 11/2006 |
| WO | 2007078281 A2 | 7/2007 |

OTHER PUBLICATIONS

International Search Report and Written Opinion for PCT-US2009/050670 Dated Dec. 16, 2009.

Communication pursuant to Article 94(3) for European Patent Application No. 13174260.3, mailed Jun. 30, 2015.

Notice of Reasons for Rejections for Japanese Patent Application No. 2011-518876, mailed Oct. 22, 2013.

Communication pursuant to Article 94(3) for European Patent Application No. 09790456.9, mailed May 2, 2013.

Third Office Action for Chinese Patent Application No. 200980127852.4, mailed Jul. 25, 2013.

Fourth Office Action for Chinese Patent Application No. 200980127852.4, mailed Jan. 3, 2014.

Fifth Office Action for Chinese Patent Application No. 200980127852.4, mailed Jul. 20, 2014.

* cited by examiner

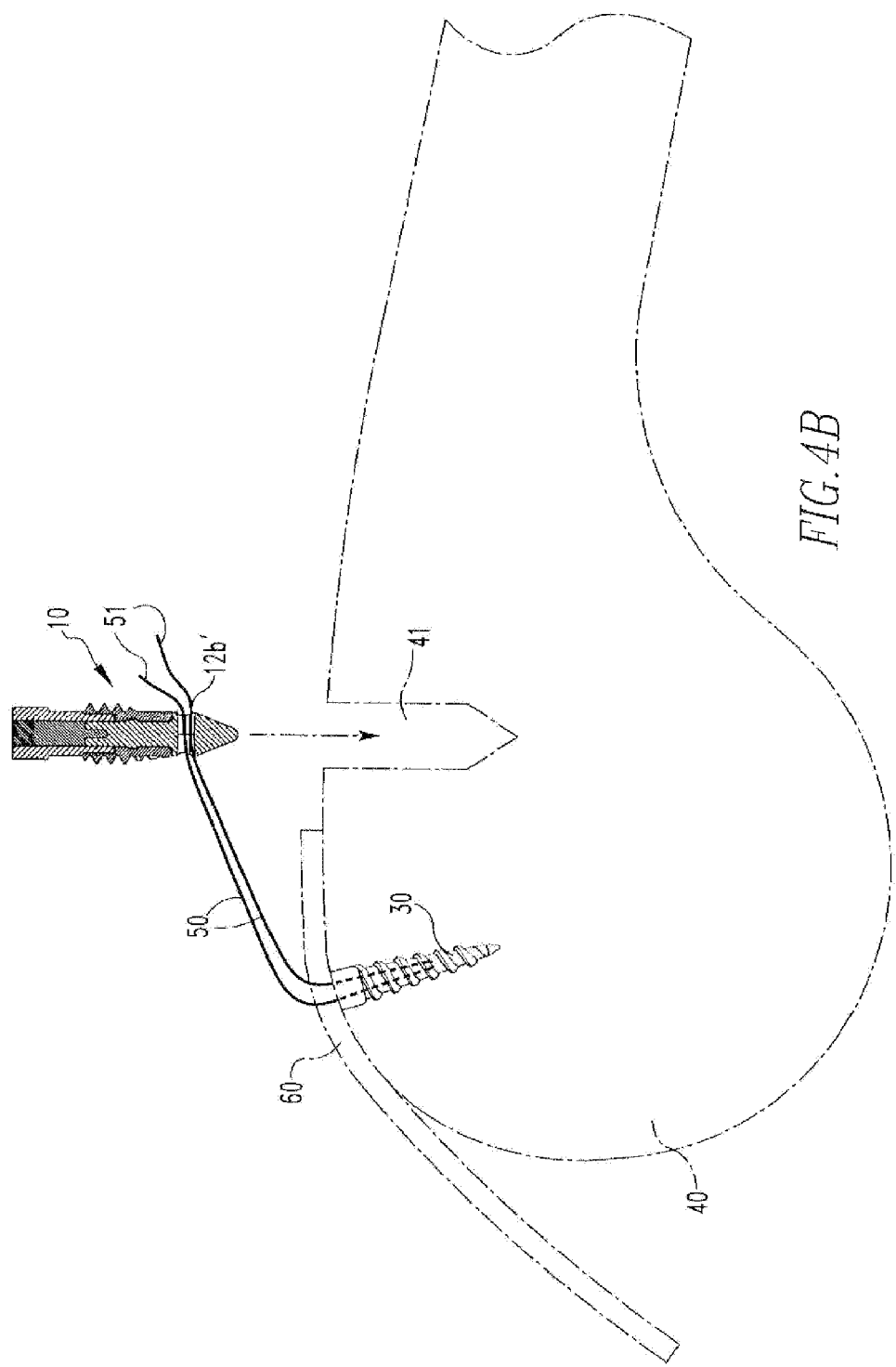

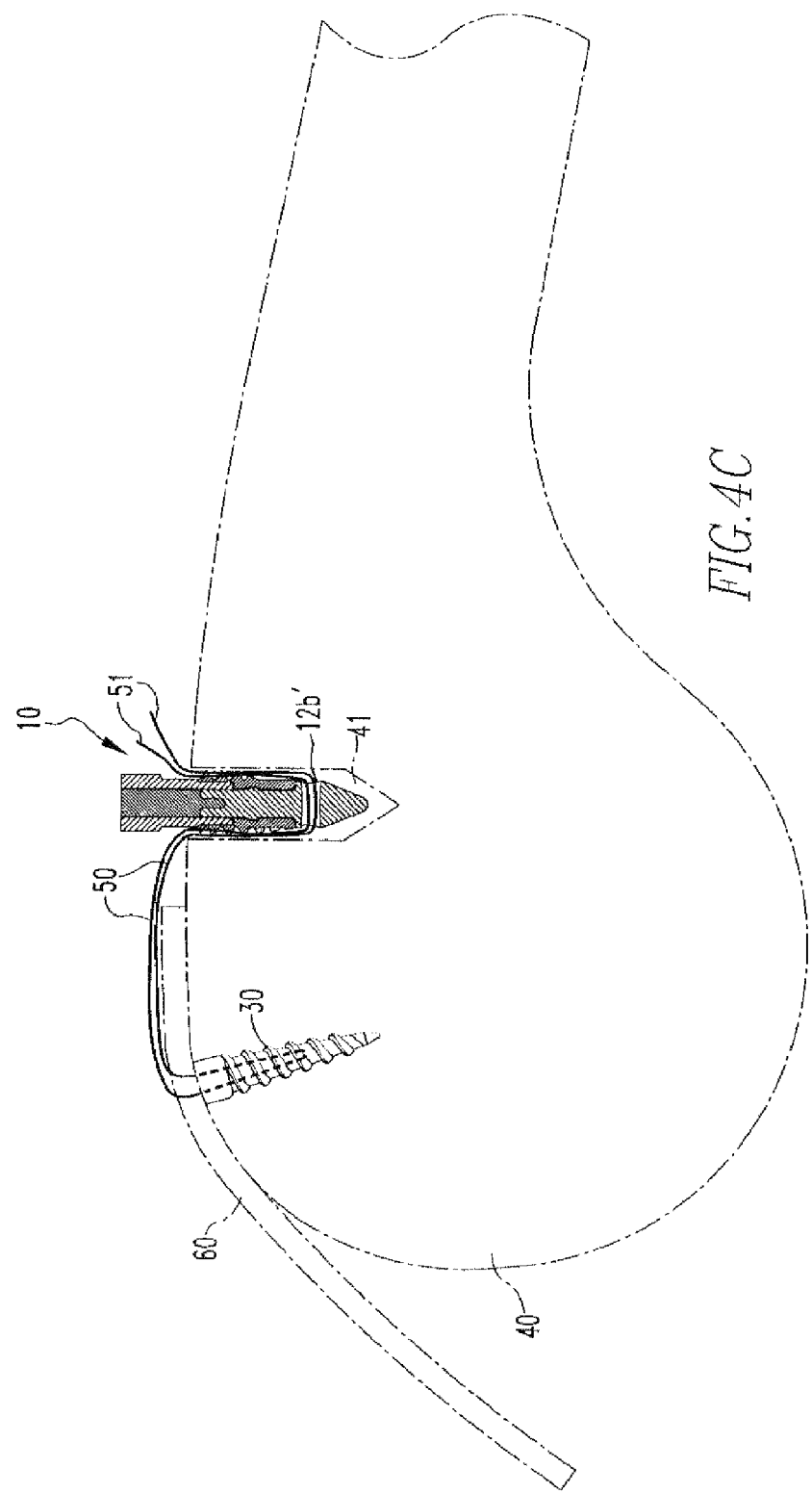

ANCHOR

RELATED APPLICATION

This application is a division of U.S. patent application Ser. No. 13/736,586, filed Jan. 8, 2013, entitled, "Anchor", which is a divisional of U.S. patent application Ser. No. 12/503,394, filed Jul. 15, 2009, entitled, "Anchor", which claims priority to U.S. Patent Application No. 61/081,438 filed on Jul. 17, 2008, the disclosure of the aforementioned applications are incorporated herein by reference in their entirety.

BACKGROUND

Field of Technology

The present disclosure relates to the repair of soft tissue and, more importantly, an anchor for use in the repair.

Related Art

Arthroscopic procedures often require soft tissue to be reattached to bone. To achieve this, anchors are placed in the bone and sutures attached to the anchor are passed through the tissue to securely retain the tissue in place. When making a repair of soft tissue to bone, it is advantageous to have as large an area of contact between the bone and tissue as possible. Anchor points spaced from one another in rows result in a repair having a broader area of contact. A procedure, and devices for use in such procedure, that securely attaches tissue to bone using a plurality of attachment points over a large area of contact is needed.

SUMMARY

In one aspect, the present disclosure relates to an anchor. The anchor includes an outer member including a body having an inner cavity, wherein the inner cavity includes a proximal portion configured for receipt of a delivery device and a distal portion having area of increased diameter. The anchor also includes an inner member coupled to the outer member, wherein the inner member includes a proximal portion having a projection configured for receipt in the area of increased diameter and a distal portion having a transverse through hole.

In an embodiment, the outer member includes threads on an outer surface of the outer member. In another embodiment, the outer member includes longitudinal grooves on an outer surface of the member, the grooves extending a partial length of the outer member. In yet another embodiment, the proximal portion of the inner member includes an opening configured for receipt of a delivery device. In a further embodiment, the outer member rotates relative the inner member. In yet a further embodiment, the proximal portion of the inner member has a smaller diameter than the distal portion of the inner member.

In another aspect, the present disclosure relates to a delivery device including an inner shaft having a proximal portion and a distal portion, a first handle coupled to the proximal portion of the inner shaft, an outer shaft slidably engaged with the inner shaft and including a proximal portion and a distal portion, and a second handle coupled to the proximal portion of the outer shaft.

In an embodiment, the delivery device further comprises an anchor including an outer member including a body having an inner cavity, the inner cavity including a proximal portion configured for receipt of the outer haft of the delivery device and a distal portion having area of increased diameter, and an inner member coupled to the outer member, the inner member including a proximal portion having a projection configured for receipt in the area of increased diameter and a distal portion having a transverse through hole. In another embodiment, the proximal portion of the inner member includes an opening configured for receipt of the inner shaft of the delivery device.

In yet another aspect, the present disclosure relates to a method of tissue repair including inserting a first anchor into bone, the first anchor having a flexible member coupled thereto; passing the ends of the flexible member through the tissue; providing a second anchor comprising an outer member including a body having an inner cavity, the inner cavity including a proximal portion configured for receipt of the outer shaft of the delivery device and a distal portion having area of increased diameter, and an inner member coupled to the outer member, the inner member including a proximal portion having a projection configured for receipt in the area of increased diameter and a distal portion having a transverse through hole; passing the ends of the flexible member through the through hole of the of the second anchor; and advancing the second anchor into bone via both axial and rotary advancement.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIGS. 4A-4C show the anchor of FIG. 1 in use during arthroscopic tissue repair.

DETAILED DESCRIPTION OF THE EMBODIMENTS

The following description of the preferred embodiment(s) is merely exemplary in nature and is its no way intended to limit the disclosure, its application, or uses.

Figure 1:
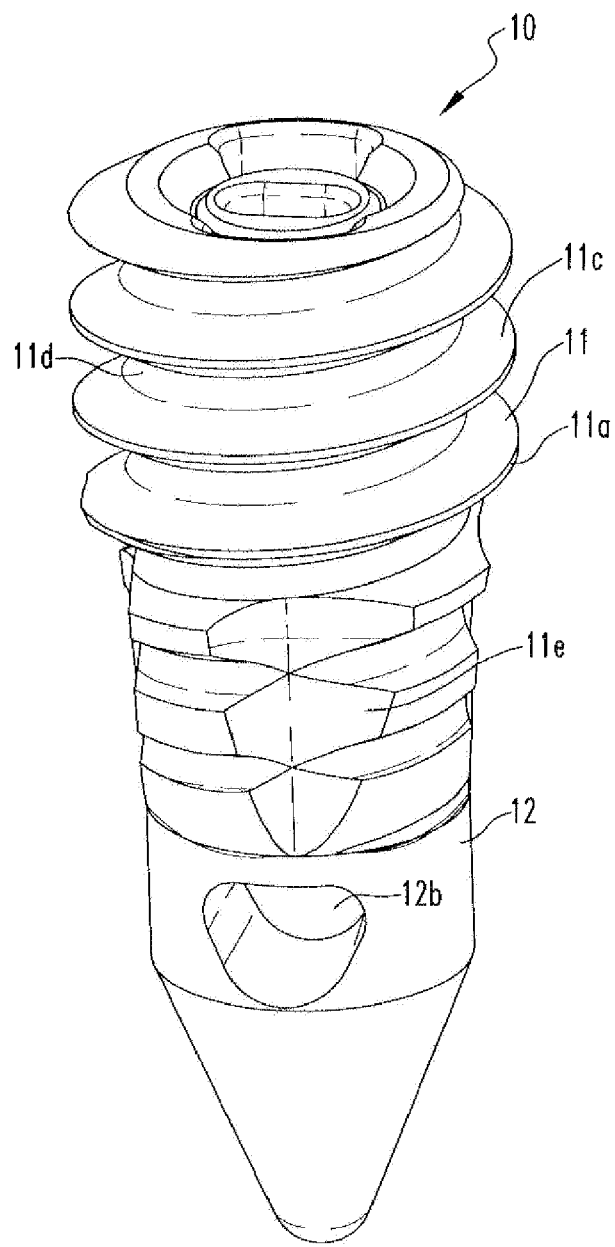
FIG. 1 shows a perspective view of an anchor of the present disclosure.
Figure 2:
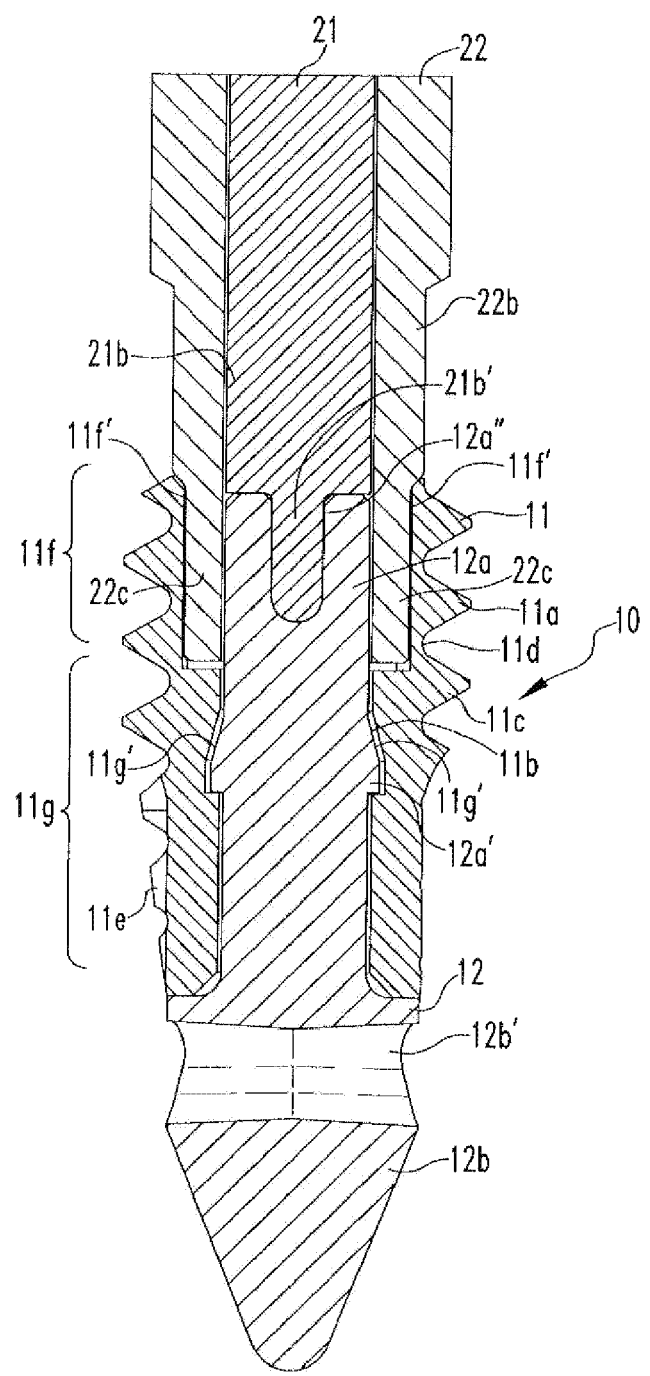
FIG. 2 shows a cross-sectional view of the anchor shown in FIG. 1.

FIGS. 1 and 2 show the anchor 10 of the present disclosure. The anchor 10 includes an outer member 11 having a body 11a and an inner cavity 11b. The body 10 includes threads 11c on an outer surface 11d of the body 11a. In addition, longitudinal grooves 11e are located on the outer surface 11d. The grooves 11e extend a partial length of the outer member 11 and intersect the threads 11e. The purpose of the grooves 11e will be further described below. The inner cavity 11b includes a proximal portion 11f and a distal portion 11g. The proximal portion 11f includes channels 11f' that are configured for receipt of a delivery device, as will be further described below. The distal portion 11g includes an area of increased diameter 11g', the purpose of which will be further described below.

The anchor 10 also includes an inner member 12 coupled to the outer member 11. The inner member 12 includes a proximal portion 12a and a distal portion 12b. The proximal portion 12a has a smaller diameter than the distal portion 12b and is located within the inner cavity 11b. A projection 12a' is located on the proximal portion 12a and is received within the area of increased diameter 11g' when the proximal portion 12a is located within the inner cavity 11b, such that the outer member 11 is rotatable relative to the inner member 12, as will be further described below. The proximal portion 12a also includes an opening 12a'' that is configured for receipt of a delivery device, as will be further described below. The distal portion 12b includes a transverse through hole 12b', for purposes to be described below.

Figure 3:
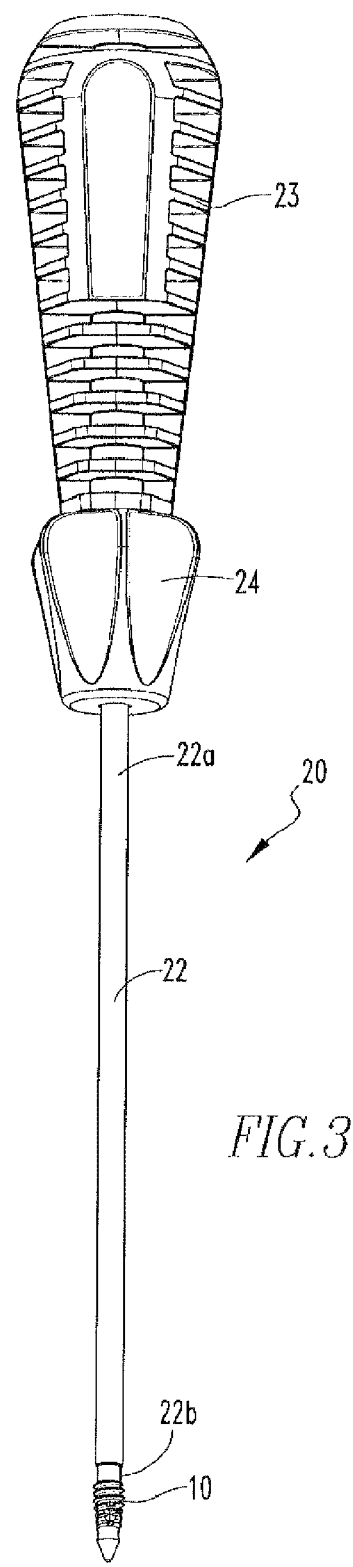
FIG. 3 shows a perspective view of the delivery device of the present disclosure.

FIG. 3 shows a delivery device 20 including an inner shaft 21 (FIG. 2), an outer shaft 22 (FIG. 2) slidably engaged with the inner shaft 21, and first and second handles 23,24 coupled to the inner and outer shafts 21,22 respectively. The inner shaft 21 includes a proximal portion (not shown) and a distal portion 21b. The distal portion 21b includes a prong 21b' that is located within the opening 12a'' of the inner member 12 when the anchor 10 is coupled to the delivery device 20. The outer shaft 22 also includes a proximal portion 22a and a distal portion 22b. The distal portion 22b includes prongs 22c, extending from the distal portion 22b and as shown in FIG. 2, that are located within the channels 11f' of the outer member 11 when the anchor 10 is coupled to the delivery device 20. In addition, the distal portion 22b includes a smaller diameter compared to the diameter of the rest of the shaft 22. This smaller diameter substantially reduces the possibility of the shaft 22b from being lodged within the bone during insertion of the anchor 10.

Figure 4A:
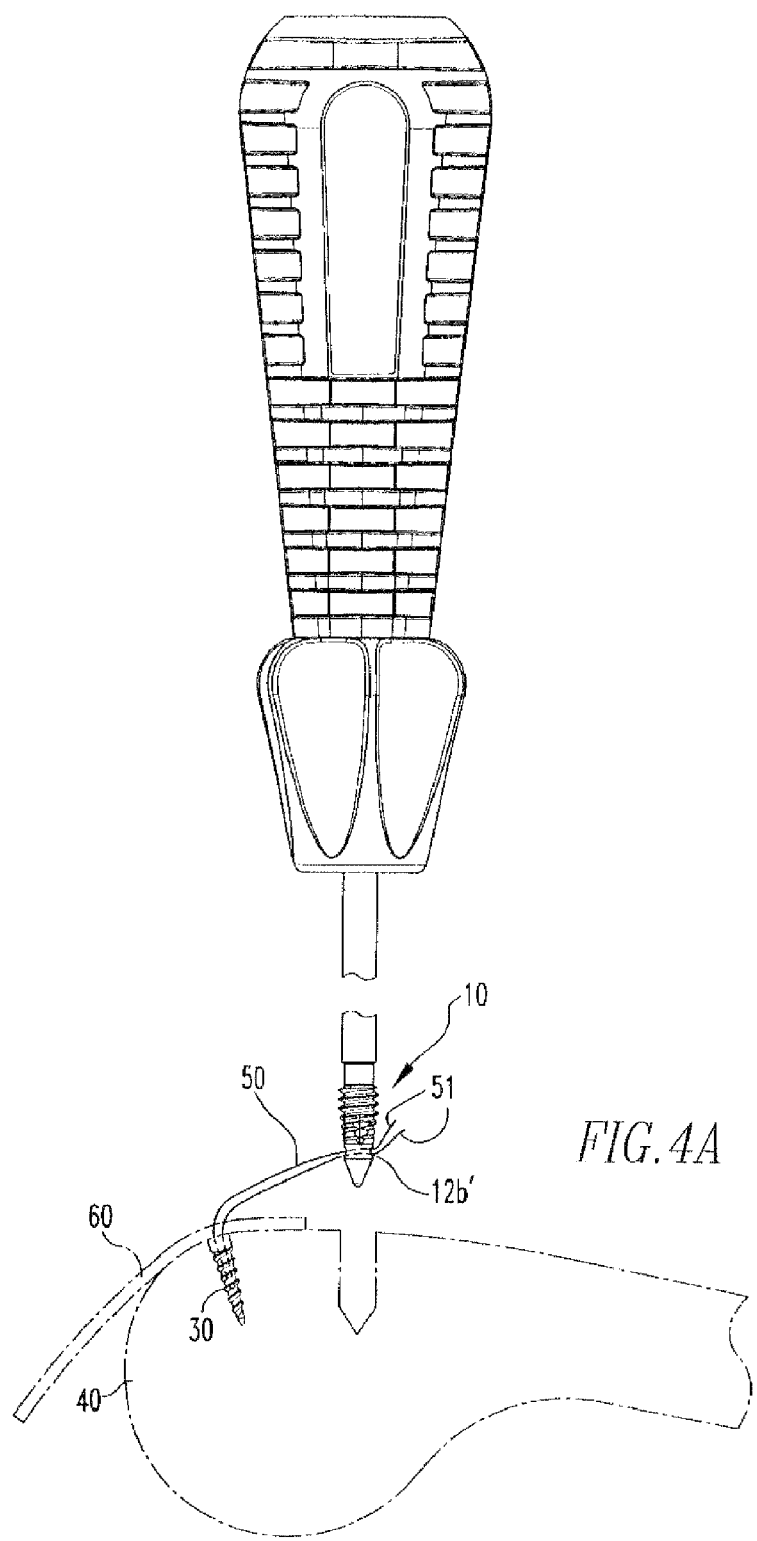

FIGS. 4A-4C show the anchor 10 in use during arthroscopic repair of the rotator cuff. FIG. 4A shows a first anchor 30 that has been inserted into the lateral aspect of a bone 40, such as a humeral bone. The anchor 30, which has a flexible member 50, such as a suture, coupled thereto is inserted into the bone 40, a soft tissue 60, such as a rotator cuff tendon, is placed on the bone 40 to be located adjacent to the anchor 30, and the ends of the flexible member 50 are placed through the soft tissue 60.

Next at least one end 51 of the flexible member 50 is passed through the transverse through hole 12b', as shown in FIGS. 4A & 4B. After the flexible member 50 is passed through the through hole, the anchor 10 is subsequently inserted into a previously drilled hole 41 in the medial aspect of the bone 40, as shown in FIG. 4C, such that the flexible member 50 is housed within the transverse through hole 12b' and the ends 51 extend out of the hole 41. The anchor 10 is advanced into the hole 41 in an axially-oriented manner by tapping on the first handle 23 until the grooves 11e are located within the hole 41 and can no longer be viewed. The second handle 24 is then used to rotate the outer member 11 relative to the inner member 12 and advance the remaining portion of the anchor 10 into the hole 41 until the entire anchor 10 is located within the bone 40 or flush with the bone 40. The delivery device 20 is subsequently disengaged from the anchor 10 and removed from the hole 41.

The shafts 21,22 include a stainless steel material, but may be made from any other metal or non-metal material that is bio-compatible and strong enough to withstand the forces that are placed on the shafts 21,22 during surgery. The shafts 21,22 may be machined, die drawn and subsequently machined, or made by any other method known to one of skill in the art. The shafts 21,22 are coupled to the handles 23,24 via a press-fit procedure. However, other methods of coupling the handles 23,24 to the shafts 21,22 are also within the scope of this disclosure. The handles 21,22 are of a non-metal material, but may be made from a metal material, and both are made via an injection molding process. However, other methods of making are also within the scope of this disclosure.

The components of the anchor 10 are made from a bioabsorbable polymer material and via an injection molding process. In addition, for the purposes of this disclosure, other methods or coupling the inner and outer members 11,12 may be used.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A method of tissue repair comprising:
   inserting a first anchor into bone, the first anchor having a flexible member coupled thereto;
   passing the ends of the flexible member through the tissue;
   providing a second anchor comprising an outer member including a body having an inner cavity, the inner cavity including a proximal portion configured for receipt of the outer shaft of a delivery device and a distal portion having area of increased diameter, and an inner member coupled to the outer member, the inner member including a proximal portion having a projection configured for receipt in the area of increased diameter and a distal portion having a transverse through hole;
   passing the ends of the flexible member through the through hole of the of the second anchor; and
   advancing the second anchor into bone via both axial and rotary advancement.

* * * * *